United States Patent
Sim et al.

(10) Patent No.: US 9,662,279 B2
(45) Date of Patent: May 30, 2017

(54) COSMETIC COMPOSITION PREPARED BY IMPREGNATION IN URETHANE FOAM

(75) Inventors: Min Kyung Sim, Yongin-si (KR); Jung Sun Choi, Yongin-si (KR); Yu Jin Kang, Yongin-si (KR); Kyung Nam Kim, Yongin-si (KR); Yeong Jin Choi, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 19 days.

(21) Appl. No.: 14/129,357

(22) PCT Filed: Jun. 25, 2012

(86) PCT No.: PCT/KR2012/004991
§ 371 (c)(1),
(2), (4) Date: Dec. 26, 2013

(87) PCT Pub. No.: WO2013/002523
PCT Pub. Date: Jan. 3, 2013

(65) Prior Publication Data
US 2014/0154295 A1    Jun. 5, 2014

(30) Foreign Application Priority Data

Jun. 27, 2011  (KR) .................. 10-2011-0062404
Jun. 25, 2012  (KR) .................. 10-2012-0067819

(51) Int. Cl.
| | | |
|---|---|---|
| A45D 34/04 | (2006.01) | |
| A61K 8/46 | (2006.01) | |
| A61K 8/87 | (2006.01) | |
| A61Q 1/02 | (2006.01) | |
| A61Q 19/00 | (2006.01) | |
| A61K 8/02 | (2006.01) | |
| A61K 8/06 | (2006.01) | |
| A61K 8/04 | (2006.01) | |
| A61Q 17/04 | (2006.01) | |

(52) U.S. Cl.
CPC ............ *A61K 8/0208* (2013.01); *A45D 34/04* (2013.01); *A61K 8/046* (2013.01); *A61K 8/064* (2013.01); *A61K 8/87* (2013.01); *A61Q 1/02* (2013.01); *A61Q 19/00* (2013.01); *A45D 2200/1018* (2013.01); *A45D 2200/1036* (2013.01); *A61K 2800/10* (2013.01); *A61K 2800/87* (2013.01); *A61Q 17/04* (2013.01)

(58) Field of Classification Search
CPC .......... A61Q 17/04; A61Q 1/02; A61Q 19/02; A61Q 1/04; A61Q 1/08; A61Q 1/10; A61K 8/0208; A61K 8/064; A61K 2800/244; A61K 2800/87; A61K 2800/88; A61K 8/0216; A61K 8/0241; A61K 8/044; A61K 8/06
See application file for complete search history.

(56) References Cited

U.S. PATENT DOCUMENTS

| | | | | |
|---|---|---|---|---|
| 6,183,729 | B1 * | 2/2001 | Noordam ................. | A61K 8/67 424/400 |
| 6,334,727 | B1 * | 1/2002 | Gueret ................... | A45D 33/00 401/190 |
| 7,416,735 | B2 * | 8/2008 | El-Nokaly ........... | A61K 8/0241 424/400 |
| 2003/0216483 | A1 * | 11/2003 | Hermann ............. | A01K 1/0152 521/50 |
| 2010/0029182 | A1 * | 2/2010 | Fukuda .................... | B24D 3/26 451/41 |
| 2011/0014254 | A1 * | 1/2011 | Choi .................... | A61K 8/0208 424/401 |

FOREIGN PATENT DOCUMENTS

| | | |
|---|---|---|
| JP | 57-24305 A | 2/1982 |
| KR | 10-2006-0024612 A | 3/2006 |
| KR | 10-2009-0100643 A | 9/2009 |

OTHER PUBLICATIONS

International Searching Authority, International Search Report of PCT/KR2012/004991 dated Jan. 30, 2013.

* cited by examiner

*Primary Examiner* — Audrea Buckley
(74) *Attorney, Agent, or Firm* — Sughrue Mion, PLLC

(57) ABSTRACT

The present invention relates to a cosmetic composition in which a W/O (water in oil) cosmetic composition with low viscosity is packaged in an airless container, and more specifically, to a cosmetic composition with low viscosity which enhances the stability of easily-separable low viscosity materials and improves user convenience by impregnating the W/O cosmetic composition with low viscosity into a urethane foam and packaging the composition in the airless container.

11 Claims, 2 Drawing Sheets

_(1)_

COSMETIC COMPOSITION PREPARED BY IMPREGNATION IN URETHANE FOAM

CROSS REFERENCE TO RELATED APPLICATIONS

This application is a National Stage of International Application No. PCT/KR2012/004991 filed Jun. 25, 2012, claiming priority based on Korean Patent Application Nos. 10-2011-0062404 filed Jun. 27, 2011 and 10-2012-0067819 filed Jun. 25, 2012 the contents of all of which are incorporated herein by reference in their entirety.

TECHNICAL FIELD

The present invention relates to a low-viscosity cosmetic composition which is prepared by impregnating an easily separable low-viscosity water-in-oil (W/O) emulsion composition into a urethane foam and packaging the impregnated 10 urethane foam in an airless container in order to increase the stability of the cosmetic composition and improve the convenience of use of the cosmetic composition.

BACKGROUND ART

Generally, cosmetic compositions that are required to have long-acting properties are prepared as water-in-oil (WO) type emulsions having oil as an external phase in order to increase their resistance to sweat or water. Oil-in-water (O/W) type cosmetic compositions have an advantage in that they give a fresh feeling upon application to the skin compared to water-in-oil type cosmetic compositions, but have a shortcoming in that they are easily washed out with sweat or water, even though studies have been continuously conducted to increase the water resistance thereof. On the other hand, water-in-oil type cosmetic compositions have excellent long-acting properties compared to oil-in-water cosmetic compositions, but have shortcomings in that they give a heavy feeling and are sticky. Such shortcomings can be somewhat overcome by reducing the viscosity of the cosmetic compositions, but it is generally known that water-in oil type cosmetic compositions have low emulsion stability compared to oil-in-water cosmetic compositions. Particularly, water-in-oil type cosmetic products with low viscosity have a problem in that the stability of the products is low because the internal water phase is separated from the external oil phase when the cosmetic products are stored in containers for a long period of time during circulation. Due to this problem, there is a limit to reducing the viscosity of water-in-oil type cosmetic products.

For this reason, a water-in-oil type cosmetic composition is adjusted to low viscosity and placed in a tube or a deep-pump container according to the intended use thereof. Even when the external oil phase of this cosmetic product is separated from the internal water phase, it is mixed with the internal water phase when the cosmetic product is shaken by the user before use. However, this cosmetic product is inconvenient to use and also leaves a large amount of residue that causes a complaint. For this reason, cosmetic products that do not need to be shaken have been developed, and in the process of preparing these cosmetic products, the viscosity of the cosmetic products is increased to about 10000 cps in order to increase the stability thereof.

DISCLOSURE OF INVENTION

Technical Problem

In order to stabilize a low-viscosity water-in-oil cosmetic composition having a light touch feeling and good long-acting properties, the present inventors have attempted to develop a novel fluid type cosmetic product, deviating from conventional methods of either adding an increased amount of an emulsifying agent giving a bad touch feeling or increasing the viscosity of cosmetic compositions.

To achieve the above object, the present invention provides a low-viscosity fluid cosmetic composition which is prepared by impregnating an easily-separable low-viscosity water-in-oil cosmetic composition into a urethane foam and packaging the impregnated urethane foam in an airless container in order to increase the stability of the cosmetic composition and improve the convenience of use of the cosmetic composition.

The present invention also provides an airless cosmetic container containing a urethane foam impregnated with a cosmetic composition.

Solution to Problem

The present invention provides an airless container package type formulation containing a urethane foam impregnated with a low-viscosity water-in-oil emulsion composition that contains an oil phase component, an emulsifying agent, an organic or inorganic UV-blocking agent, a pigment and a water phase component.

Advantageous Effects of Invention

According to the present invention, a low-viscosity water-in-oil cosmetic composition which can be stabilized by packaging in an airless pump container so that it can be used until empty while satisfying all properties, including formulation stability, fresh touch feeling and long-acting properties.

MODE FOR THE INVENTION

Figure 1:
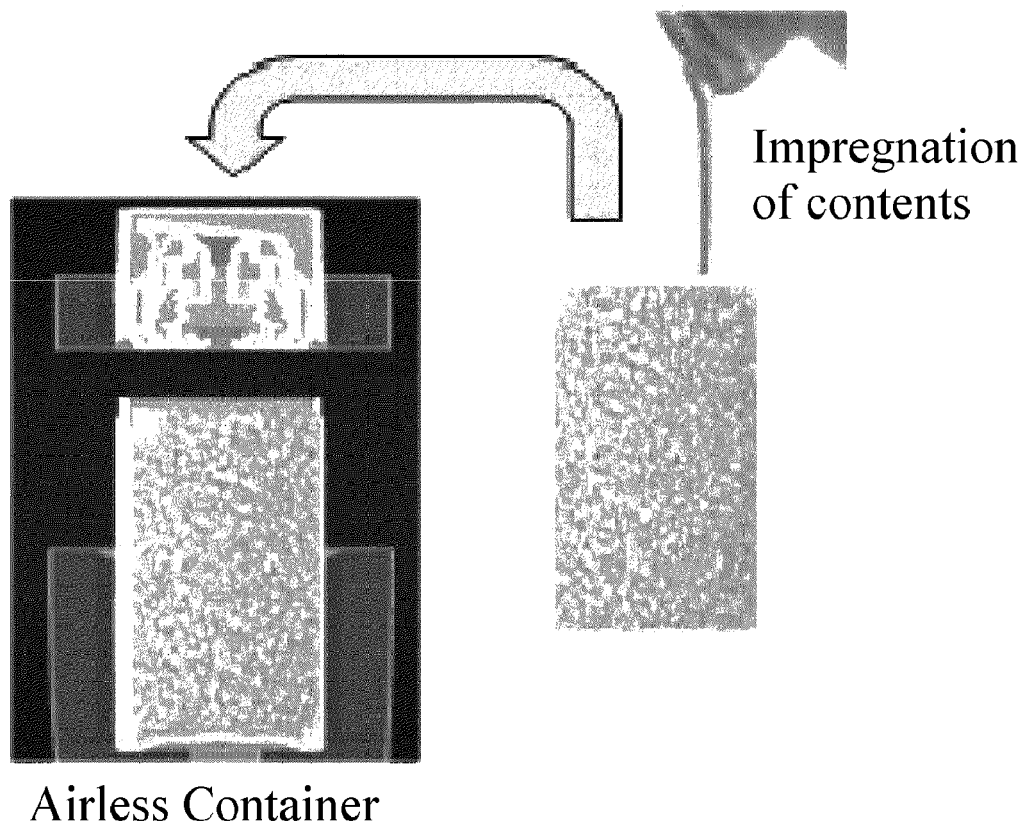
FIG. 1 is a photograph showing impregnation of contents into urethane foam.
Figure 2:
FIG. 2 is a photograph showing a cosmetic container containing a cosmetic composition of the present invention.
Figure 2:
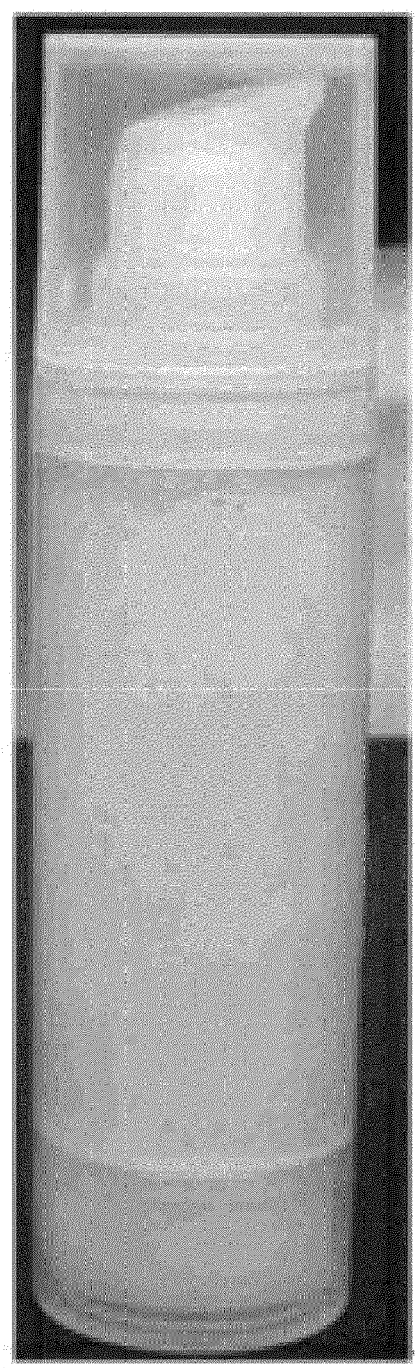

The oil phase component that is used in the composition of the present invention is one or more selected from among vegetable oils, including rosehip oil, peach seed oil, meadowfoam seed oil and sunflower seed oil; synthetic esters or hydrocarbons, including dicaprylyl carbonate, squalane, neopentyl glycol diheptanoate, tocopheryl acetate, trioctanoin, $C_{12\text{-}15}$ alkyl benzoate, $C_{12\text{-}15}$ alkyl ethylhexanoate, octyldodecyl myristate, tricaprylin, octyldodecyl stearoyl stearate, isotridecyl isononanoate, bis-hydroxyethoxypropyl dimethicone, caprylic/capric triglyceride, polyglyceryl-2 tri-isostearate, diisostearyl malate, cetyl octanoate, and dipentaerythrite fatty acid ester; silicone oils, including phenyl trimethicone, cyclomethicone, and dimethicone; etc. The oil phase component is contained in an amount of 20 to 80 wt % based on the total weight of the composition. If the content of the oil-phase component in the composition is less than 20 wt %, the composition will have poor stability or excessively high viscosity, and thus it will impart a heavy feeling to the skin and be sticky, thus deteriorating the usability of the composition. If the content of the oil-phase component in the composition is more than 80 wt %, the composition will have poor stability.

The emulsifying agent that is used in the present invention is preferably a nonionic surfactant that has a low hydrophilic lipophilic balance (HLB) of 1 to 6 so as to be able to provide a water-in-oil emulsion. Specifically, the emulsifying agent that is used in the present invention may be one or more selected from among cyclopentasiloxane and PEG/PPG-18/18 dimethicone, glycol stearate, sorbitan sesquioleate, glyceryl oleate, glycol distearate, propylene glycol monostearate, glyceryl stearate, sorbitan stearate, PEG-30 dipolyhydroxystearate, PEG-10 dimethicone, cyclopentasiloxane/PEG.PPG-19.19 dimethicone, sorbitan isostearate, lauryl PEG.PPG-18.18 methicone, cetyl PEG.PPG-10.1 dimethicone, lauryl PEG-9 polydimethylsiloxyethyl dimethicone, etc. The emulsifying agent is contained in an amount of 0.01 to 10 wt % based on the total weight of the composition. If the content of the emulsifying agent in the composition is less than 0.01 wt %, an emulsion will not be formed or the stability of the composition will be poor, and if the content of the emulsifying agent is more than 10 wt %, the composition will be sticky and can severely give out an offensive odor due to the emulsifying agent.

The UV-blocking agent that is used in the present invention may be selected from among organic UV-blocking agents and inorganic UV-blocking agents, which can be used alone or in a mixture of two or more thereof. Specifically, examples of organic UV-blocking agents that may be used in the present invention include octyl methoxycinnamate, octyl salicylate, octocrylene, octyl trizaone, butyl methoxydibenzoylmethane, oxybenzone, methoxycinnamate, menthyl anthranilate, isoamyl-P-bis-ethylhexyloxyphenol methoxyphenyl triazine, methylene bis-benzotrizolyl tetramethylbutylphenol, etc. Examples of inorganic UV-blocking agents that may be used in the present invention include titanium dioxide having a mean particle size of 5 to 100 nm, zinc oxide having a mean particle size of 5 to 300 nm, etc. Herein, as the mean particle size of inorganic UV-blocking agents increases, the whitening of the composition will become more severe upon application to the skin, and thus the product value of the composition will be reduced. However, if the particle size of inorganic UV-blocking agents is too small, they can penetrate into the skin to cause skin irritation. Accordingly, the mean particle size of inorganic UV-blocking agents is preferably 300 nm or less in view of the whitening phenomenon, and is preferably 10 to 50 nm in view of whitening together with skin irritation.

The UV-blocking agent is contained in an amount of 1 to 35 wt % based on the total weight of the composition. If the content of the UV-blocking agent is less than 1 wt %, the UV-blocking effect thereof will be insignificant, and if the content of the UV-blocking agent is more than 35 wt %, the whitening and glossiness of the composition will become severe or the composition can cause skin irritation.

The pigment that is used in the present invention is a component excluding the inorganic UV-blocking agent and may be one or more selected from among polymethylmethacrylate (PMMA), silica, nylon, polyurethane, ultramarine, iron oxide, pearl, synthetic mica, mica, sericite and boron nitride. The pigment is contained in an amount of 0.5 to 20 wt % based on the total weight of the composition. If the content of the pigment in the composition is less than 0.5 wt %, the touch feeling, color or stability of the composition will be insignificant, and if the pigment content is more than 20 wt %, it will excessively increase the viscosity of the composition, thus imparting a hard feeling to the skin and reducing the stability of the emulsion.

The water-phase component that is used in the present invention may be one or more selected from among purified water, propylene glycol, 1,3-butylene glycol, and glycerin and is contained in an amount of 20-60 wt % based on the total weight of the composition. If the content of the water-phase component in the composition is less than 20 wt %, the viscosity of the composition will be excessively low so that the stability of the composition will be reduced, and if the content of the water-phase component is more than 60 wt %, the viscosity of the composition will be excessively increased.

In addition to the above-described components, one or more selected from among fragrances and other additives may further be added to the composition. Additives that are used in the present invention may be functional materials such as arbutin or adenosine.

The water-in-oil emulsion composition of the present invention has a low viscosity of 2000 to 5000 cps. If the viscosity of the water-in-oil emulsion composition is smaller than 2000 cps, separation between the oil phase and water phase of the emulsion composition will occur so that the composition will be difficult to stabilize even when being impregnated into a urethane foam, and if the viscosity is higher than 5000 cps, the composition will give a heavy feeling to the skin, and thus will have a low product value and will not differ from conventional products.

The low-viscosity water-in-oil emulsion composition of the present invention may be used as a flowable or fluid formulation such as lotion, essence, sun milk lotion, liquid foundation, liquid BB cream or the like.

The cosmetic composition of the present invention is impregnated into polyurethane foam which is contained in an airless container. More specifically, the urethane foam is contained in the airless container in a non-compressed state, and when pressure is applied from the bottom by pumping at the top, the content (composition) is dispensed from the container while the urethane foam is compressed. FIG. 1 shows an airless cosmetic container containing a urethane foam.

A urethane foam which is impregnated with the cosmetic composition of the present invention is preferably open-cell type foam, because closed-cell type foam has closed pores and thus cannot be impregnated with the UV-blocking composition.

The urethane foam, which is used in the present invention is open-cell type urethane foam, preferably has a hardness of 10 to 70 as measured by a durometer hardness tester (type F; manufactured by ASKER). If the urethane foam is excessively soft, the water-in-oil emulsion cosmetic composition impregnated in the urethane foam will excessively flow out when being pumped, and if the urethane foam is excessively hard, the water-in-oil emulsion cosmetic composition will not easily flow out.

Mode for Invention

Hereinafter, the present invention will be described in further detail with reference to examples. However, these examples are for illustrative purposes only and are not intended to limit the scope of the present invention in any way.

Reference Examples 1 and 2

According to the components and contents shown in Table 1 below, makeup cosmetic compositions of Reference Examples 1 and 2, which are examples of the water-in-oil emulsion cosmetic composition according to the present invention, were prepared.

Specifically, oil-phase components, a UV-blocking agent, an emulsifying agent and a thickener were mixed with each other, heated to 80° C. and stirred to form a uniform mixture. A pigment was added to the mixture which was then uniformly stirred to obtain an oil phase solution. Meanwhile, in a separate mixer, water-phase components were mixed with each other, heated to 80° C. and stirred to form a water-phase solution. The water-phase solution obtained by heating the water-phase components to 80° C. was added slowly to the oil phase solution, and the mixture was emulsified using a homomixer. The emulsion was cooled to 50° C., and then skin protecting components and fragrance were added the emulsion which was then cooled.

TABLE 1

| | | Components | Reference Example 1 (wt %) | Reference Example 2 (wt %) |
|---|---|---|---|---|
| Oil phase components | Oily component | Ozokerite | 0.1 | 1.0 |
| | | Dicaprylyl carbonate | 10.00 | 10.00 |
| | UV-blocking agent | Octyl methoxycinnamate | 7.000 | 7.000 |
| | Thickener | Disteardimonium hectorite | 0.20 | 1.50 |
| | Oily component | Decamethyl-cyclopent asiloxane | 16.00 | 16.00 |
| | Emulsifying agent | Sorbitan sesquioleate | 2.000 | 2.000 |
| | | Lauryl PEG.PPG-18.18 methicone | 1.500 | 1.500 |
| | Pigment | Polymethyl-methacrylate | 5.00 | 5.00 |
| | | Titanium dioxide/iron oxide | 7.00 | 7.00 |
| Water-phase components | | Water | To 100 | To 100 |
| | Moisturizer | Glycerin | 8.000 | 8.000 |
| | Emulsion stabilizer | Salt | 1.00 | 1.00 |
| | | Fragrance | 0.200 | 0.200 |
| | Total | | 100.000 | 100.000 |

Test Example 1

Test for Viscosity, Spreadability and Formulation Stability

The viscosity, spreadability and formulation stability of the water-in-oil emulsion makeup cosmetic compositions of Reference Examples 1 and 2 were tested using different containers and package methods. In Examples 1 and 2 corresponding to Reference Examples 1 and 2, respectively, each of the compositions were impregnated into urethane foam having a hardness of 40 as measured with an ASKER hardness tester (type F) and was stored in an airless container. In Comparative Examples 1 corresponding to Reference Examples 1 and Comparative Examples 2 to corresponding to Reference Examples 2, respectively, each of the compositions was stored in a general dip tube pump container.

The viscosity of each of the compositions (Reference Examples 1 and 2) was measured using a rotational rheometer (DV III, Brookfield) after allowing each composition to stand at 30° C. for 24 hours. The light spreadability and application uniformity of each of the compositions (Reference Examples 1 and 2) were measured by evaluating the touch feeling of each composition on a five-point scale by 40 women expert panels (25 to 40 years old of age) and averaging the evaluated values.

In addition, the emulsion stability of each of the compositions was determined by observing oil separation and emulsion breakdown in each of the compositions while storing each composition under the constant temperature conditions of 45° C. and 55° C. for 7 days. The results of the tests are shown in Table 2 below.

TABLE 2

| | Viscosity | Spread-ability | Application uniformity | After 7 days at 45° C. | After 7 days at 55° C. |
|---|---|---|---|---|---|
| Comparative Example 1 | 4000 cps | 5 | 5 | Separated | Separated |
| Example 1 | 4000 cps | 5 | 5 | Stable | Stable |
| Comparative Example 2 | 15000 cps | 3 | 3 | Stable | Some bubbles occurred |
| Example 2 | 15000 cps | 3 | 3 | Stable | Stable |

Evaluation Criteria for Five-Point Scale

5: very light/very uniform; 4: light/uniform; 3: moderate; 2: not light/not uniform; and 1: not very light/not very uniform.

It could be seen that the compositions of Example 1 and Comparative Example 1 had high viscosity, and thus were lightly spread and showed high application uniformity, but the composition of Comparative Example 1 showed oil separation within 7 days, and the composition of Example 1 was stable for more than 7 days. The compositions of Example 2 and Comparative Example 2 had a relatively high viscosity of 15000 cps and were generally stable, but the light spreadability or application uniformity thereof was low, suggesting that there is a limit to the spreadability of the compositions of Example 2 and Comparative Example 2.

Test Example 2

Test for Pumping Preference According to Hardness of Urethane Foam

The composition of Reference Example 1 was impregnated into urethane foams having various hardness values, and then pumping preference and dispense stability were compared between the urethane foam. In the test, 40 women were allowed to use impregnated urethane foams of Examples 3 to 5 and to select one having excellent pumping and dispense characteristics from the urethane foams. The results of the test are shown in Table 3 below.

TABLE 3

| | Kind of impregnated content | Hardness (ASKER hardness, type F) of a urethane foam impregnated with content | Pumping preference (%) | Dispense stability (%) |
|---|---|---|---|---|
| Example 3 | Reference Example 1 | 5 | 20 | 10 |
| Example 4 | Reference Example 1 | 80 | 5 | 10 |
| Example 5 | Reference Example 1 | 40 | 75 | 80 |

As can be seen in Table 3 above, the content-impregnated urethane foam having a hardness of 40 showed the highest preference. When the hardness of the urethane foam was 5, pumping was easily achieved, spattering frequently occurred upon dispense due to the low density of the content, and when the hardness was as high as 80, pumping required a considerable force, and the amount of dispense was too small.

Test Example 3

Examination of Preference According to Type of Container

The composition of Reference Example 1 was impregnated into urethane foam having a hardness of 40 (as measured with an ASKER hardness tester (type F), and the urethane foam was placed in an airless container (Example 6). Further, the composition was placed in each of a general dip tube pump (Comparative Example 3), a tube (Comparative Example 4 and a blow container (Comparative Example 5). The difference in preference between Example 6 and Comparative Examples 3 to 5 was examined. The dip tube pump container and the blow container contained a conventional ball in order to solve the separation of the low-viscosity content into phases and were shaken before use. In the test, 40 women were allowed to use the samples of Example 6 and Comparative Examples 3 to 5 by dispense until empty for 3 months and to select one sample having the best usability. The results of the test are shown in Table 4 below.

TABLE 4

| | Preference (%) |
|---|---|
| Example 6 | 70 |
| Comparative Example 3 | 20 |
| Comparative Example 4 | 0 |
| Comparative Example 5 | 10 |

As can be seen in Table 4 above, the case in which the composition impregnated into urethane foam was packaged in the airless container (Example 6) showed a significantly high preference compared to the cases in which the composition was packaged in other containers. The reasons for non-preference of the dip tube pump container were that the tube pump container needed to be shaken before every use and could not be used until empty. In the case of the tube container, the separation of the content occurred from about one month after the start of use so that the tube container could not be used, and thus the preference was 0%. The reasons for non-preference of the blow container containing the ball were that the blow container needed to be shaken before every use and that the dispense port became dirty with the flow of the content and also that it was difficult to control the amount of dispense. However, the reasons for preference of the airless pump container containing the urethane foam were that the airless pump container did not need to be shaken before every use and could be used until empty.

Test Example 4

Formulation Stability According to Hardness of Urethane Foam 15 g of the cosmetic composition (viscosity: 4,000 cps) of Reference Example 1 was impregnated into urethane foams (thickness: 10 mm) having a hardness of 5, 10, 15, 25, 35, 45, 55, 65, 70 or 80 as measured with an ASKER hardness tester (type F), and the stability thereof was tested. The results of the test are shown in Table 5 below.

TABLE 5

| Hardness | After 10 days at 45° C. | After 5 days of 8-hour cycle [45° C.→30° C.→ freezing (−10° C.)] | After 2 hours at 50° C. |
|---|---|---|---|
| 5 | Separated | Separated | Separated |
| 10 | Stable | Stable | Stable |
| 15 | Stable | Stable | Stable |
| 25 | Stable | Stable | Stable |
| 35 | Stable | Stable | Stable |
| 45 | Stable | Stable | Stable |
| 55 | Stable | Stable | Stable |
| 65 | Stable | Stable | Stable |
| 70 | Stable | Stable | Stable |
| 80 | Stable | Stable | Stable |

As can be seen from the results in Table 5 above, in the case in which the hardness of the urethane foam was lower than 5, the formulation was separated and became unstable as time and temperature changed, whereas in the case in which the hardness of the urethane foam impregnated with the cosmetic composition ranged from 10 to 70 as described in the present invention, the formulation was stably maintained even when temperature and time changed. In the case in which the hardness of the urethane foam was higher than 70, separation of the formulation did not occur, but the urethane foam was not effective in providing packability and dispensability for the cosmetic composition, as can be seen in the following test examples 5 and 6.

Test Example 5

Packability According to Hardness of Urethane Foam 15 g of the makeup cosmetic composition (viscosity: 4,000 cps) of Reference Example 1 was impregnated into urethane foams (diameter: 48 mm, and thickness: 10 mm) having a hardness of 5, 10, 15, 20, 25, 30, 35, 40, 45, 50, 55, 60, 70 or 80 as measured with an ASKER hardness tester (type F), and the time (sec) required to pack 15 g of the cosmetic composition into the urethane foam was measured. The results of the measurement of the time (packability) are shown in Table 6 below.

TABLE 6

| | Hardness of urethane foam | | | | | | | | | | | | | |
|---|---|---|---|---|---|---|---|---|---|---|---|---|---|---|
| | 5 | 10 | 15 | 20 | 25 | 30 | 35 | 40 | 45 | 50 | 55 | 60 | 70 | 80 |
| Packability (sec) | 40 | 20 | 18 | 17 | 14 | 13 | 5 | 6 | 5 | 4 | 4 | 15 | 21 | 35 |

As can be seen in Table 6 above, when the urethane foam impregnated with the cosmetic composition had a hardness of 5, it had a poor ability to support the content, and thus the content flowed out downward when packing the composition. The packability for 15 g of the cosmetic composition into the urethane foam having a hardness of 5 was as long as 40 seconds. Meanwhile, in the case of the urethane foam having an excessively high hardness of 80, the packability was as long as 35 seconds.

Accordingly, it can be seen that the hardness that shows actually acceptable packability is in the range of 10 to 70 and that a hardness of 35 to 55 shows packability shorter than 5 sec.

Test Example 6

Dispensability According to Hardness of Urethane Form

A puff was brought into contact with urethane foam (48 mm in diameter and 10 mm in thickness), impregnated with 15 g of the cosmetic composition (viscosity: 4000 cps) of Reference Example 1, under a pressure of 412 Pa, and the amount of the cosmetic composition dispensed on the puff was measured to determine dispensability. As used herein, the term "dispensability" is defined as the amount (g) of the cosmetic composition dispensed on the puff each time when the puff is brought into contact with the urethane foam. The foams used in this Test Example were 14 urethane foams impregnated with the cosmetic composition of Reference Example 1 and having hardness values of 5, 10, 15, 20, 25, 30, 35, 40, 45, 50, 55, 60, 70 and 80, respectively, as measured with an ASKER hardness tester (type F). The results of measurement of the dispensability are shown in Table 7 below.

nated with the cosmetic composition was 5, the dispensability was as much as 2.2 g, suggesting that it is difficult to apply the cosmetic composition uniformly to the skin and that sanitary problems and unpleasant feelings are caused due to severe contamination of the puff. In the case in which the hardness of the urethane foam was 80, the dispensability was as small as 0.1 g, suggesting that the cosmetic composition cannot be applied in a sufficient amount, and thus is inconvenient to use.

Reference Examples 3 to 7

According to the components and contents shown in Table 8 below, makeup cosmetic compositions of Reference Examples 3 to 7 were prepared, which had viscosities of 1000, 2000, 3500, 5000 and 6000 cps. The compositions were prepared in the same manner as described in Reference Examples 1 and 2. Specifically, oil-phase components, a UV-blocking agent, an emulsifying agent and a thickener were mixed with each other, heated to 80° C. and stirred to form a uniform mixture. A pigment was added to the mixture which was then uniformly stirred to obtain an oil phase solution. Meanwhile, in a separate mixer, water-phase components were mixed with each other, heated to 80° C. and stirred to form a water-phase solution. The water-phase solution obtained by heating the water-phase components to 80° C. was added slowly to the oil phase solution, and the mixture was emulsified using a homomixer. The emulsion was cooled to 50° C., and then skin protecting components

TABLE 7

| | Hardness of urethane foam | | | | | | | | | | | | | |
|---|---|---|---|---|---|---|---|---|---|---|---|---|---|---|
| | 5 | 10 | 15 | 20 | 25 | 30 | 35 | 40 | 45 | 50 | 55 | 60 | 70 | 80 |
| Dispensability (g) | 2.20 | 1.30 | 1.20 | 1.00 | 0.80 | 0.70 | 0.43 | 0.44 | 0.50 | 0.46 | 0.48 | 0.33 | 0.30 | 0.10 |

As can be seen from the results in Table 7 above, in the case in which the hardness of the urethane foam impregand fragrance were added the emulsion which was then cooled.

TABLE 8

| | | Components | Ref. Ex. 3 (wt %) | Ref. Ex. 4 (wt %) | Ref. Ex. 5 (wt %) | Ref. Ex. 6 (wt %) | Ref. Ex. 7 (wt %) |
|---|---|---|---|---|---|---|---|
| Viscosity (cps) | | | 1000 | 2000 | 3500 | 5000 | 6000 |
| Oil-phase components | Oily component | Dicaprylyl carbonate | 10.00 | 10.00 | 10.00 | 10.00 | 10.00 |
| | UV blocking agent | Octyl methoxycinnamate | 7.000 | 7.000 | 7.000 | 7.000 | 7.000 |
| | Thickener | Disteardimonium hectorite | 0.05 | 0.10 | 0.15 | 0.25 | 0.30 |
| | Oily component | Decamethylcyclopentasiloxane | 16.00 | 16.00 | 16.00 | 16.00 | 16.00 |

TABLE 8-continued

|  |  | Components | Ref. Ex. 3 (wt %) | Ref. Ex. 4 (wt %) | Ref. Ex. 5 (wt %) | Ref. Ex. 6 (wt %) | Ref. Ex. 7 (wt %) |
|---|---|---|---|---|---|---|---|
|  | Emulsifying agent | Sorbitan sesquioleate | 2.000 | 2.000 | 2.000 | 2.000 | 2.000 |
|  |  | Lauryl PEG.PPG-18.18 methicone | 1.500 | 1.500 | 1.500 | 1.500 | 1.500 |
|  | Pigment | Polymethylmethacrylate | 5.00 | 5.00 | 5.00 | 5.00 | 5.00 |
|  |  | Titanium dioxide/iron oxide | 7.00 | 7.00 | 7.00 | 7.00 | 7.00 |
| Water-phase components |  | Water | To 100 | To 100 | To 100 | To 100 | To 100 |
|  | Moisturizer | Glycerin | 8.000 | 8.000 | 8.000 | 8.000 | 8.000 |
|  | Emulsion stabilizer | Salt | 1.00 | 1.00 | 1.00 | 1.00 | 1.00 |
|  |  | Fragrance | 0.200 | 0.200 | 0.200 | 0.200 | 0.200 |
| Total |  |  | 100.000 | 100.000 |  |  | 100.000 |

Test Example 7

Packability of Urethane Foam According to Viscosity of UV-Blocking Cosmetic Composition 15 g of each of the cosmetic compositions of Reference Examples 3 to 7, which had viscosities of 1000, 2000, 3500, 5000 and 6000 cps as shown in Table 8 above, was impregnated into urethane foam (diameter: 48 mm, and thickness: 10 mm) having a hardness of 40 as measured with an ASKER hardness tester (type F), and the time (sec) required to pack 15 g of the cosmetic composition into the urethane foam was measured. The results of measurement of the time as "packability" are shown in Table 9 below.

TABLE 9

|  | Reference Example 3 | Reference Example 4 | Reference Example 5 | Reference Example 6 | Reference Example 7 |
|---|---|---|---|---|---|
| Viscosity (cps) | 1000 | 2000 | 3500 | 5000 | 6000 |
| Packability (sec) | 4 | 4 | 6 | 8 | 22 |

As can be seen from the results in Table 9 above, when the viscosity of the makeup cosmetic composition was as low as 1000, the packability was as short as 4 seconds, phase separation in the makeup cosmetic composition occurred due to low emulsion stability, and the cosmetic composition flowed out from the bottom of the urethane foam without impregnation into the foam. When the viscosity of the cosmetic composition was as high as 6000, the packability was 22 seconds, which was about 3 to 6 times longer than a packability of 4 to 8 seconds at optimum hardness. Thus, it can be seen that the cosmetic composition having a viscosity of 2000-5000 cps as described in the present invention shows optimum packability without phase separation.

Test Example 8

Dispensability of Urethane Foam According to Viscosity of UV-Blocking Cosmetic Composition A puff was brought into contact with urethane foam (48 mm in diameter and 10 mm in thickness), impregnated with 15 g of the cosmetic composition (viscosity: 4000 cps) of Reference Examples 3 to 7 and having a viscosity of 40 as measured with an ASKER hardness tester (type F), under a pressure of 412 Pa, and the amount of the cosmetic composition dispensed on the puff was measured to determine dispensability. As used herein, the term "dispensability" is defined as the amount (g) of the cosmetic composition dispensed on the puff each time when the puff is brought into contact with the urethane foam. The results of the measurement are shown in Table 10 below.

TABLE 10

|  | Reference Example 3 | Reference Example 4 | Reference Example 5 | Reference Example 6 | Reference Example 7 |
|---|---|---|---|---|---|
| Viscosity (cps) | 1000 | 2000 | 3500 | 5000 | 6000 |
| Dispensability (g) | 1.20 | 0.48 | 0.44 | 0.40 | 2.00 |

As can be seen from the results in Table 10 above, in the case in which the urethane foam was impregnated with the composition of Reference Example 3 having a low viscosity of 1000 cps, the amount of the cosmetic composition dispensed on the puff was as much as 1.20 g (about 3 times the optimum amount of 0.40 g), suggesting that it is difficult to apply the cosmetic composition uniformly to the skin and that sanitary problems and unpleasant feelings are caused due to severe contamination of the puff. In addition, in the case in which the urethane foam was impregnated with the cosmetic composition of Reference Example 7 having a high viscosity of 6000 cps, the cosmetic composition was not sufficiently packed in the foam, and the amount of cosmetic composition that floated to the upper surface of the urethane foam increased, and thus the dispensability increased to 2.00 g (about 5 times the optimum dispensability of 0.40 g), suggesting that the cosmetic composition is difficult to apply uniformly to the skin and is applied locally, and thus is inconvenient to use.

The invention claimed is:
1. A cosmetic composition application system comprising:
an airless single chamber container;
a urethane foam; and
a liquid cosmetic composition having a viscosity of 2,000-4,000 cps,
wherein the airless single chamber container is a pump dispenser;
wherein the urethane foam has a hardness of 10-70 and is packed inside the chamber of the container; and
wherein the liquid cosmetic composition is impregnated into the urethane foam.
2. The cosmetic composition application system of claim 1, wherein the liquid cosmetic composition is a water-in-oil type cosmetic composition.

3. The cosmetic composition application system of claim 1, wherein the liquid cosmetic composition contains, based on the total weight of the composition, 20 to 80 wt % of an oil-phase component, 0.01 to 10 wt % of an emulsifying agent, 1 to 35 wt % of a UV-blocking agent, 0.5 to 20 wt % of a pigment and 20 to 60 wt % of a water-phase component.

4. The cosmetic composition application system of claim 3, wherein the oil-phase component is one or more selected from the group consisting of vegetable oils, synthetic ester oils, hydrocarbon oils and silicone oils.

5. The cosmetic composition application system of claim 3, wherein the emulsifying agent is a nonionic surfactant having a hydrophilic lipophilic balance of 1 to 6.

6. The cosmetic composition application system of claim 3, wherein the pigment is one or more selected from the group consisting of polymethylmethacrylate, silica, nylon, polyurethane, ultramarine, iron oxide, pearl, synthetic mica, mica, talc, sericite, and boron nitride.

7. The cosmetic composition application system of claim 3, wherein the water-phase component is one or more selected from the group consisting of purified water, propylene glycol, 1,3-butylene glycol, and glycerin.

8. The cosmetic composition application system of claim 2, wherein the liquid cosmetic composition is a composition for blocking UV rays.

9. The cosmetic composition application system of claim 2, wherein the liquid cosmetic composition is selected from the group consisting of lotion, essence, sun milk lotion, liquid base, liquid foundation, and liquid BB cream.

10. The cosmetic composition application system of claim 1, wherein the urethane foam has a hardness of 25, 30, 35, 40, 45, 50 or 55.

11. The cosmetic composition application system of claim 1, wherein the liquid cosmetic composition has a viscosity of 2000, 3500, or 4000 cps.

* * * * *